(12) United States Patent
Tsai et al.

(10) Patent No.: US 9,677,985 B2
(45) Date of Patent: Jun. 13, 2017

(54) APPARATUS AND METHOD FOR INSPECTING FILTERING CARTRIDGE

(71) Applicant: TAIWAN SEMICONDUCTOR MANUFACTURING CO., LTD., Hsinchu (TW)

(72) Inventors: Ming-Han Tsai, Taichung (TW); Yi-Ming Chen, New Taipei (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 510 days.

(21) Appl. No.: 14/276,545

(22) Filed: May 13, 2014

(65) Prior Publication Data

US 2015/0330885 A1 Nov. 19, 2015

(51) Int. Cl.
*G01N 15/06* (2006.01)
*H01L 21/673* (2006.01)
*G01N 15/08* (2006.01)

(52) U.S. Cl.
CPC ....... *G01N 15/06* (2013.01); *H01L 21/67393* (2013.01); *G01N 2015/084* (2013.01)

(58) Field of Classification Search
CPC ............. G01N 15/06; G01N 2015/084; G01N 2015/0046; G01N 2015/1486; H01L 21/67393; H01L 21/67389; H01L 21/67769
USPC ............. 73/28.01, 24.03, 38, 61.71; 206/710
See application file for complete search history.

(56) References Cited

U.S. PATENT DOCUMENTS

| 8,356,526 B2 * | 1/2013 | Favre ................ H01L 21/67017 73/864.33 |
| 2003/0110944 A1 * | 6/2003 | Wu ..................... B01D 46/0067 95/63 |
| 2005/0269241 A1 * | 12/2005 | Brooks ............. H01L 21/67353 206/710 |
| 2010/0294397 A1 * | 11/2010 | Kishkovich ............... G03F 1/66 141/66 |
| 2011/0168613 A1 * | 7/2011 | van Savooijen ..... B01D 35/147 210/133 |
| 2014/0166799 A1 * | 6/2014 | Davis, Jr. ........... B65H 75/4434 242/382.1 |

* cited by examiner

*Primary Examiner* — Hezron E Williams
*Assistant Examiner* — Marrit Eyassu
(74) *Attorney, Agent, or Firm* — Maschoff Brennan

(57) ABSTRACT

An apparatus applicable to a storage container is provided and includes a filtering cartridge, a gas supply device and a particle counter. The filtering cartridge is configured to be disposed on the storage container. The filtering cartridge includes a flexible housing and a filter. The flexible housing has a first portion and a second portion opposite to the first portion. The flexible housing includes a gas inlet, a first gas outlet and a second gas outlet. The gas inlet is disposed on the first portion. The first gas outlet is disposed on the first portion. The second gas outlet is disposed on the second portion and connected to the storage container. The filter is disposed over the second gas outlet. The gas supply device is connected to the gas inlet, thereby purging gas into the flexible housing. The particle counter is connected to the first gas outlet.

20 Claims, 4 Drawing Sheets

APPARATUS AND METHOD FOR INSPECTING FILTERING CARTRIDGE

BACKGROUND

Semiconductor integrated circuit fabrication facilities ("Fabs") are highly automated. An automated material handling system (AMHS) is used to transport semiconductor wafers between various process tools. The wafers are generally held in a storage container such as a front opening unified pod (FOUP). Nitrogen and other inert gases are used to prevent oxidation of wafers in the FOUP. When nitrogen and other inert gases are purged into the FOUP, some particles in the nitrogen and inert gases may also be introduced into the FOUP and cause damage to the wafers. Therefore, a filtering cartridge is disposed on the FOUP for preventing the particles from entering the FOUP.

The filtering cartridge has a limited service life. If the filtering cartridge is damaged, the particles in the filtering cartridge may enter the FOUP. Therefore, the filtering cartridge is required to be inspected and cleaned or replaced when the amount of particles therein reaches to a certain amount. Conventionally, the filtering cartridge is visually and manually inspected by an operator, thus resulting in a lot of labor costs. On the other hand, the conventional manual particle inspection is not linked to a statistical process control (SPC) system, and thus the SPC system lacks of timely particle information in the FOUP to perform quality control.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1A:
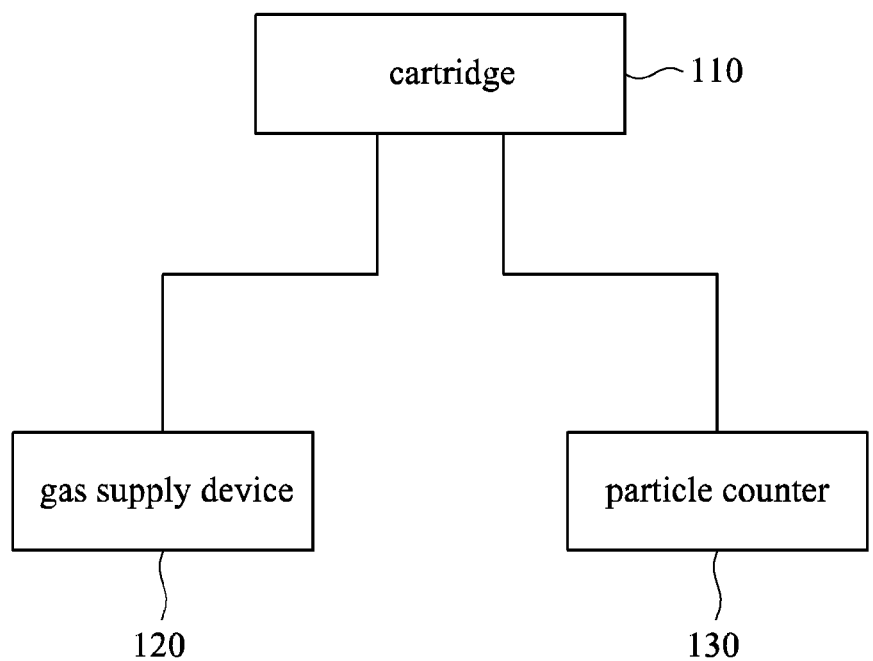
FIG. 1A is a schematic block diagram of an apparatus in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Embodiments of the present disclosure provide an apparatus applicable to a storage container (such as a FOUP). The apparatus includes a filtering cartridge, a gas supply and a particle counter. The number of the particles in the filtering cartridge is measured by the particle counter. Therefore, labor costs can be reduced.

Embodiments of the present disclosure provide a method for use in an automated material handling system (AMHS) to inspect a filtering cartridge of a storage container automatically.

According to various embodiments of the present disclosure, the method may obtain the number of the particles in the filtering cartridge, and use a statistical process control (SPC) system with the number of the particles in the filtering cartridge to control the cleanness of the filtering cartridge.

FIG. 1A is a schematic block diagram of an apparatus 100 in accordance with some embodiments. As shown in FIG. 1A, the apparatus 100 includes a filtering cartridge 110, a gas supply device 120 and a particle counter 130.

Figure 1B:
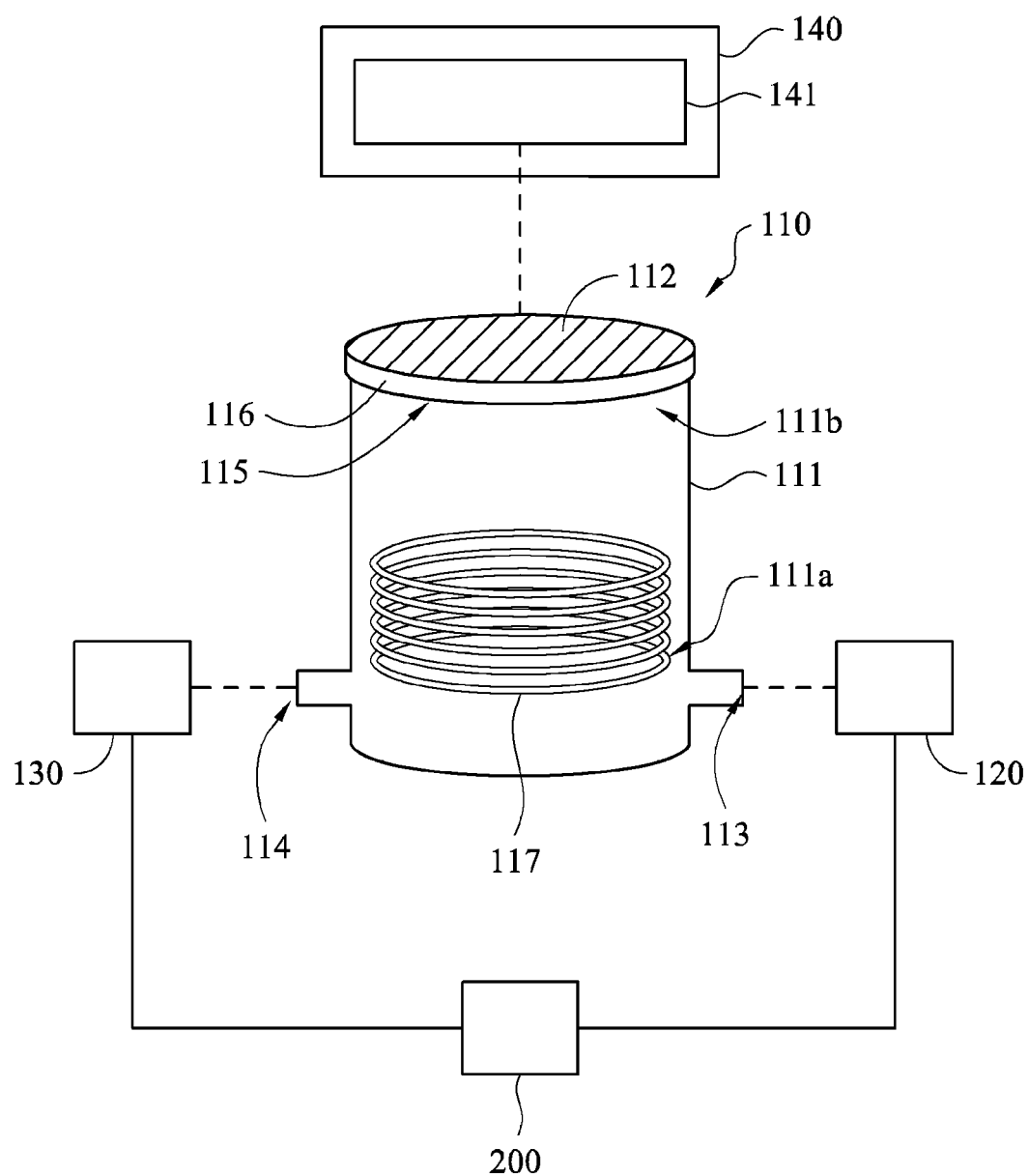
FIG. 1B is a schematic diagram of an apparatus in accordance with various embodiments.

FIG. 1B is a schematic diagram of an apparatus 100 in accordance with various embodiments. As shown in FIG. 1B, the filtering cartridge 110 is configured to be disposed on a storage container 140, such as a front opening unified pod (FOUP), a mask pod or a reticle pod. In various embodiments, the storage container 140 has a pod 141 for holding wafers, masks or reticles. The filtering cartridge 110 includes a flexible housing 111 and a filter 112.

As shown in FIG. 1B, the flexible housing 111 has a first portion 111a and a second portion 111b. The second portion 111b is located opposite to the first portion 111a. In some embodiments, the flexible housing 111 is cylindrical. The flexible housing 111 includes a gas inlet 113, a first gas outlet 114, and a second gas outlet 115. The gas inlet 113 is disposed on the first portion 111a, thereby being connected to the gas supply device 120. The first gas outlet 114 is disposed on the first portion 111a. In some embodiments, the first gas outlet 114 is located opposite to the gas inlet 113. The particle counter 130 is connected to the first gas outlet 114, thereby measuring the number of the particles in flexible housing 111 of the filtering cartridge 110. The second gas outlet 115 is disposed on the second portion 111b and connected to the storage container. The filter 112 is disposed over the second gas outlet 115. In some embodiments, the filter has a bore diameter in 0.3 µm. In certain embodiments, the filtering cartridge 110 may further include an o-ring 116. The o-ring 116 surrounds the filter 112 for fixing the filter 112.

In some embodiments, the apparatus 100 is applied to use the gas supply device 120 purging gas into the flexible housing 111 from the gas inlet 113, as shown in FIG. 1B. In various embodiments, the gas supply device 120 purges nitrogen gas, a clean dry air (CDA) or an extreme clean dry air (XCDA) into the flexible housing 111. Thereafter, the first gas outlet 114 is closed using a valve and the second gas outlet 115 is opened. The flexible housing 111 is compressed and the gas in the flexible housing 111 is moved into the storage container through the filter 112. Therefore, particles in the gas can not move into the storage container because of the filter 112. In alternative embodiments, the gas supply device 120 purges nitrogen gas, a clean dry air (CDA) or an extreme clean dry air (XCDA) into the flexible housing 111. Thereafter, the second gas outlet 115 is closed using a valve and the first gas outlet 114 is opened. The flexible housing 111 is compressed and the gas in the flexible housing 111 is moved into the particle counter 130 through the first gas outlet 114. Therefore, the particle counter 130 can be used to measure the number of the particles in flexible housing 111 of the filtering cartridge 110.

In some embodiments, the filtering cartridge 110 may further include a spring 117, as shown in FIG. 1B. In certain embodiments, the spring 117 is formed form stainless steel. The spring 117 is disposed in the flexible housing 111. When the flexible housing 111 is compressed for providing the gas into the storage container 140 or the particle counter 130, the spring 117 provides a rebound force to flexible housing 111 for recovering the shape of the flexible housing 111.

Figure 2:
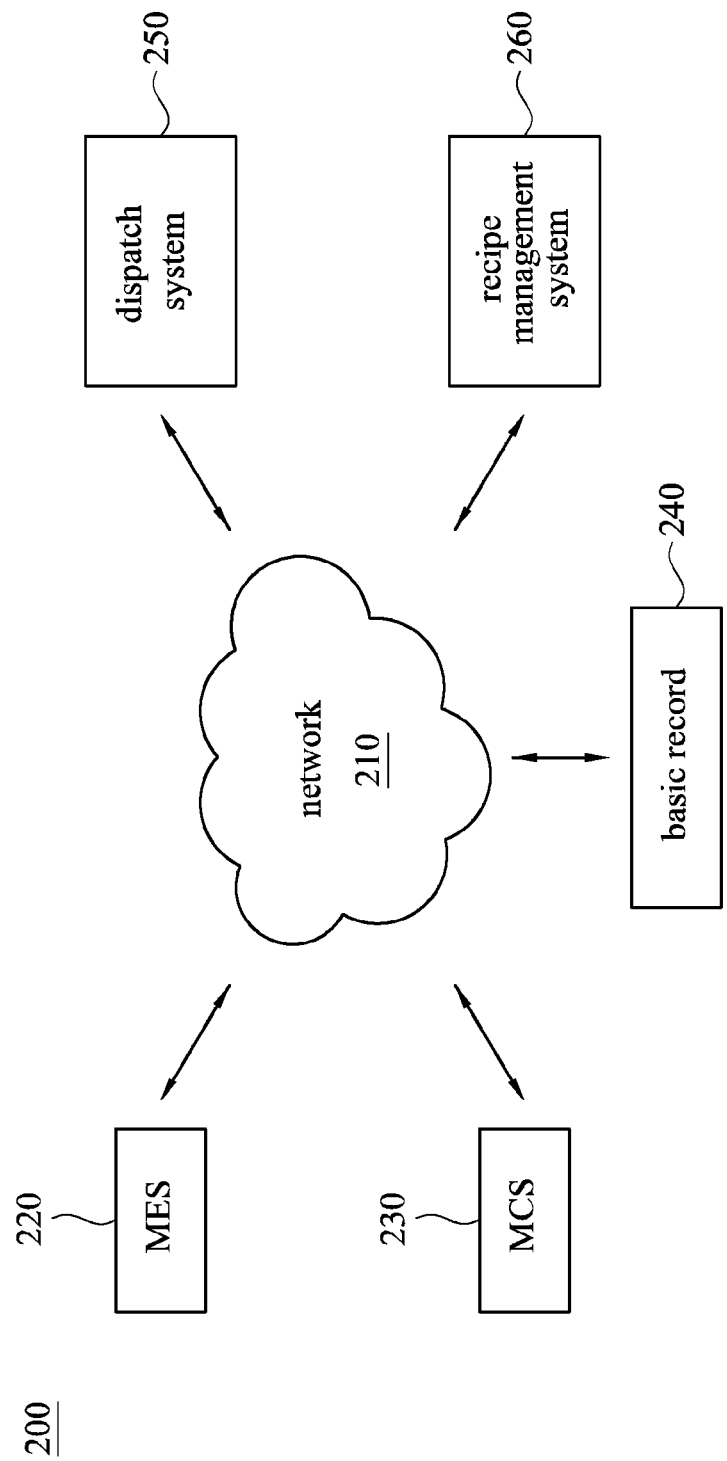
FIG. 2 is a schematic block diagram of a computer integrated manufacturing system in accordance with some embodiments.

FIG. 2 is a schematic block diagram of a computer integrated manufacturing system 200 in accordance with some embodiments. As shown in FIG. 1B and FIG. 2, the gas supply device 120 and the particle counter 130 may be electrically connected to a computer integrated manufacturing (CIM) system 200. The number measured by the particle counter 130 may be transmitted to a computer integrated manufacturing (CIM) system 200. In some embodiments, the CIM system 200 provides a complete automation of manufacturing Fabs, with all processes functioning under computer control. The CIM system 200 includes various sub-systems coupled together through a network 210 such as an intranet or the Internet. The CIM system 200 includes a manufacturing execution system (MES) 220 designed for overseeing the manufacture of semiconductor products, assigning inventory, moving inventory, scheduling tools, and other proper tasks. The CIM system 200 also includes a material control system (MCS) 230 designed for controlling material transportation and other material handling among process tools and/or among manufacturing sites. The CIM system 200 includes a basic record (BR) 240 that is a centralized system for defining a unified process flow (also referred to as process flow definition system, or PFDS). The BR 240 may be designed additionally for defining a portable data package to a mobile object such as a wafer. The CIM system 200 further includes a dispatch system 250 designed for dispatching products and other mobile objects among processing tools and manufacturing sites or facilities. The CIM system 200 further includes recipe management system 260 designed for managing and maintaining various processing recipes associated with various processing tools and various products. The CIM system 200 may further include other components for managing, coordinating, and maintaining various manufacturing tools, products, processing recipes, material control, and other manufacturing related tasks. For example, the CIM system 200 may further include a database for keeping and maintaining various manufacturing related information such as wafer or lot history, tool history, work-in-progress, and yield data.

In some embodiments, MCS 230 is used for implementing Automated Material Handling System (AMHS) activities. Automated Material Handling Systems (AMHSs; not shown) are developed to move and track storage containers 140 (such as FOUPs) that are routed through a manufacturing facility or bay. The AMHS systems may include stockers (also referred to as material storage and retrieval systems), interbay transport devices, and intrabay transport devices. Interbay transport devices move storage containers from one stocker to another as well as between bays. Intrabay transport allows movement of a storage container directly to the production equipment either from a stocker or from another production equipment in the bay. Automated interbay and intrabay transport vehicles are often referred to as automatic guided vehicles (AGVs), rail guided vehicles (RGVs), or any type of overhead transport/overhead hoist transport (OHT), and overhead vehicles (OHVs).

Figure 3:
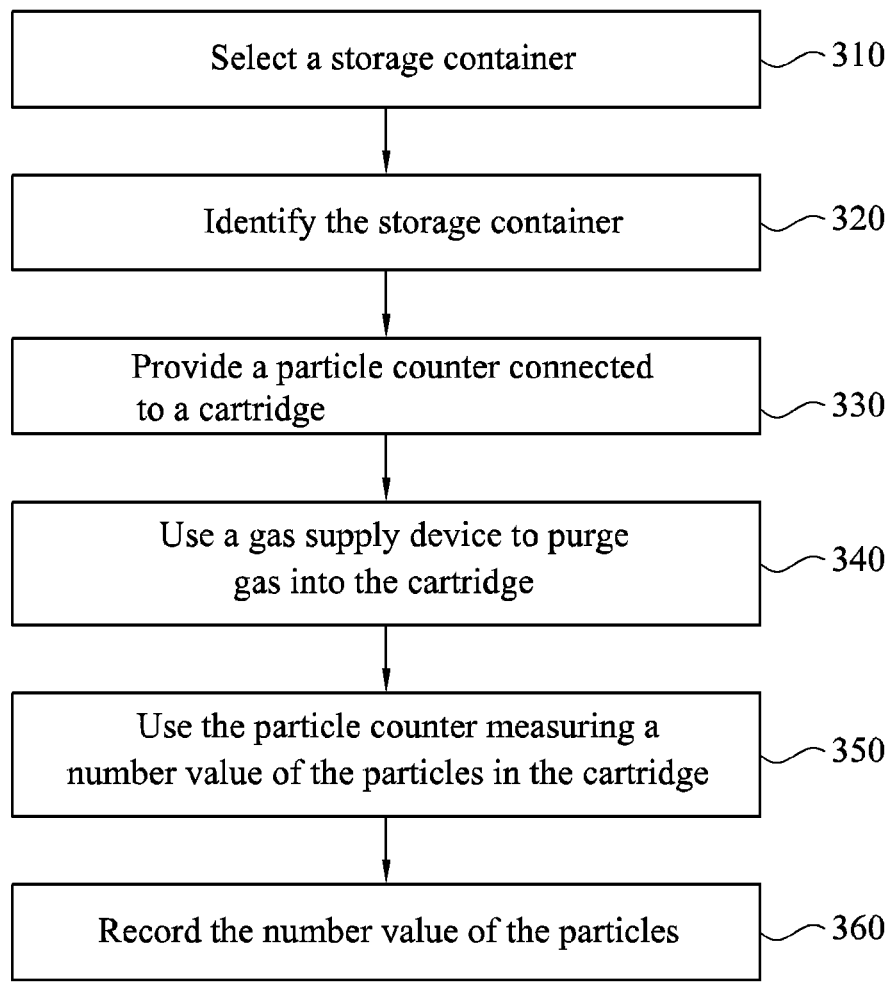
FIG. 3 is a schematic flow chart of a method for inspecting a filtering cartridge of a storage container in accordance with some embodiments.

In some embodiments, an inspecting method can be performed using the CIM system 200. FIG. 3 is a schematic flow chart of a method for inspecting a filtering cartridge 110 of a storage container 140 in accordance with some embodiments. As shown in FIG. 1A to FIG. 3, the method 300 begins at operation 310, the CIM system 200 selects a storage container 140. In some embodiments, the CIM system 200 selects one of the storage containers 140 in an AMHS stocker. At operation 320, the CIM system 200 identifies the storage container 140 by, for example, scanning an identifying mark of the storage container 140. In some embodiments, the identifying mark is a barcode or a radio-frequency identification (RFID). At operation 330, a particle counter 130 is connected to a filtering cartridge 110, in which the filtering cartridge 110 is disposed on the storage container 140. In some embodiments, the storage container 140 is a FOUP, and the filtering cartridge 110 is connected into the pod 141 of the storage container 140. At operation 340, the CIM system 200 sends a signal to the gas supply device 120, thereby purging gas into the filtering cartridge 110 for agitating particles in the filtering cartridge 110. In some embodiments, the gas includes nitrogen gas, CDA or XCDA. At operation 350, the CIM system 200 sends a signal to the particle counter 130 for measuring the number of the particles in the filtering cartridge 110. At operation 360, the BR 240 of the CIM system 200 is used to record the number of the particles.

In some embodiments, after the operation 360 of recording the number of the particles, the CIM system 200 determines the cleanness of the filtering cartridge 110 according to the number of the particles and a predetermined number. If the number is smaller than the predetermined number, the filtering cartridge 110 is determined to be clean. In some embodiments, the cleanness of the filtering cartridge 110 is determined by using a statistical process control (SPC) system, thereby controlling the cleanness of the filtering cartridge 110. In some embodiments, the number of the particles is timely collected and linked to the SPC system, and a SPC chart is produced by the SPC system. The SPC chart can be used for tracking and analyzing manufacturing process variations thereby performing quality control timely.

In some embodiments, the method 300 can be performed repeatedly by the AMHS, thereby inspecting plural storage containers 140 automatically. In general, it takes only about 40 seconds to perform the method 300 for inspecting a storage container 140, and labor costs and time can be greatly reduced.

In accordance with some embodiments, the present disclosure discloses an apparatus applicable to a storage container. The apparatus includes a filtering cartridge, a gas supply device and a particle counter. The filtering cartridge is configured to be disposed on the storage container. The filtering cartridge includes a flexible housing and a filter. The flexible housing has a first portion and a second portion opposite to the first portion. The flexible housing includes a gas inlet, a first gas outlet and a second gas outlet. The gas inlet is disposed on the first portion. The first gas outlet is disposed on the first portion. The second gas outlet is disposed on the second portion and connected to the storage container. The filter is disposed over the second gas outlet. The gas supply device is connected to the gas inlet, thereby purging gas into the flexible housing. The particle counter is connected to the first gas outlet.

In accordance with certain embodiments, the present disclosure discloses a storage container. The storage container includes a pod, a filtering cartridge, a gas supply device and a particle counter. The filtering cartridge includes a flexible housing and a filter. The flexible housing has a first portion and a second portion opposite to the first portion. The flexible housing includes a gas inlet, a first gas outlet and a second gas outlet. The gas inlet is disposed on the first portion. The first gas outlet is disposed on the first portion. The second gas outlet is disposed on the second portion and connected to the pod. The filter is disposed over the second gas outlet. The gas supply device is connected to the gas inlet, thereby purging gas into the flexible housing. The particle counter is connected to the first gas outlet.

In accordance with alternative embodiments, the present disclosure discloses a method. In this method, a storage container is selected. The storage container is identified. A particle counter is connected to a filtering cartridge, in which the filtering cartridge is disposed on the storage container. A gas supply device is used to purge gas into the filtering cartridge for agitating particles in the filtering cartridge. The particle counter is used to measure a number of the particles in the filtering cartridge. The number is recorded.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An apparatus applicable to a storage container, the apparatus comprising:
   a filtering cartridge configured to be disposed on the storage container, the filtering cartridge comprising:
      a flexible housing having a sidewall, a first end, and a second end opposite to the first end, wherein the sidewall is located between the first end and the second end, the flexible housing comprising:
         a gas inlet disposed on the sidewall of the flexible housing near the first end of the flexible housing;
         a first gas outlet disposed on the sidewall of the flexible housing near the first end of the flexible housing; and
         a second gas outlet disposed on the second end of the flexible housing and communicating with the storage container; and
      a filter disposed to cover the second gas outlet;
   a gas supply device connected to the gas inlet; and
   a particle counter located outside the flexible housing and connected to the first gas outlet.

2. The apparatus of claim 1, wherein the filtering cartridge further comprises a spring disposed in the flexible housing.

3. The apparatus of claim 1, wherein the filtering cartridge further comprises an o-ring surrounding the filter.

4. The apparatus of claim 1, wherein the gas supply device includes gas that includes nitrogen gas, clean dry air (CDA), or extreme clean dry air (XCDA).

5. The apparatus of claim 1, wherein the storage container includes a front opening unified pod (FOUP), a mask pod, or a reticle pod.

6. The storage container of claim 5, wherein the filtering cartridge further comprises a spring disposed in the flexible housing.

7. The storage container of claim 5, wherein the filtering cartridge further comprises an o-ring surrounding the filter.

8. The storage container of claim 5, wherein the gas supply device includes gas that includes nitrogen gas, CDA, or XCDA.

9. The storage container of claim 5, wherein the storage container is a front opening unified pod (FOUP), a mask pod, or a reticle pod.

10. The storage container of claim 1, wherein the filter has a bore diameter in 0.3 μm.

11. A storage container, comprising:
    a pod;
    a filtering cartridge, comprising:
       a flexible housing having a sidewall, a first end, and a second end opposite to the first end, wherein the sidewall is located between the first end and the second end, the flexible housing comprising:
          a gas inlet disposed on the sidewall of the flexible housing near the first end of the flexible housing;
          a first gas outlet disposed on the sidewall of the flexible housing near the first end of the flexible housing; and
          a second gas outlet disposed on the second end of the flexible housing and communicating with the pod; and
       a filter disposed to cover the second gas outlet;
    a gas supply device located outside the flexible housing and connected to the gas inlet; and
    a particle counter located outside the flexible housing and connected to the first gas outlet.

12. A method, comprising:
    selecting a storage container of claim 11;
    identifying the storage container;
    providing the particle counter connected to the filtering cartridge, wherein the filtering cartridge is disposed on the storage container;
    using the gas supply device to purge gas into the filtering cartridge for agitating a plurality of particles in the filtering cartridge;
    using the particle counter to measure a number of the particles in the filtering cartridge; and
    recording the number of the particles.

13. The method of claim 12, wherein selecting the storage container further comprises selecting the storage container from an automated material handling system (AMHS) stocker.

14. The method of claim 12, wherein identifying the storage container further comprises scanning an identifying mark of the storage container.

15. The method of claim 14, wherein scanning the identifying mark of the storage container further comprises scanning a barcode or a radio-frequency identification (RFID) of the storage container.

16. The method of claim 12, wherein providing the particle counter connected to the filtering cartridge further comprises the filtering cartridge disposed on a FOUP.

17. The method of claim 12, wherein using the gas supply device to purge the gas into the filtering cartridge further comprises purging nitrogen gas, CDA, or XCDA into the filtering cartridge.

18. The method of claim 12, after recording the number of the particles, further comprising determining a cleanness of the filtering cartridge according to the number of the particles.

19. The method of claim 18, wherein determining the cleanness of the filtering cartridge further comprises providing a predetermined number, wherein when the number of the particles is smaller than the predetermined number, the filtering cartridge is determined to be clean.

20. The method of claim 18, wherein determining the cleanness of the filtering cartridge using a statistical process control (SPC) system to determine the cleanness of the filtering cartridge.

* * * * *